US010866253B2

(12) United States Patent
Harrison et al.

(10) Patent No.: US 10,866,253 B2
(45) Date of Patent: Dec. 15, 2020

(54) ASSAY REACTION CONTROLLER MAGAZINE

(71) Applicant: Ventana Medical Systems, Inc., Tucson, AZ (US)

(72) Inventors: Joshua Harrison, Tucson, AZ (US); Benjamin James, St. Kilda (AU); Matthew Ketterer, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 141 days.

(21) Appl. No.: 15/681,255

(22) Filed: Aug. 18, 2017

(65) Prior Publication Data

US 2017/0343571 A1 Nov. 30, 2017

Related U.S. Application Data

(63) Continuation of application No. PCT/EP2016/053850, filed on Feb. 24, 2016.

(60) Provisional application No. 62/126,283, filed on Feb. 27, 2015.

(51) Int. Cl.
| | | |
|---|---|---|
| *G01N 35/00* | (2006.01) | |
| *G01N 1/31* | (2006.01) | |
| *B01L 9/00* | (2006.01) | |
| *G01N 33/487* | (2006.01) | |
| *G02B 21/34* | (2006.01) | |

(52) U.S. Cl.
CPC .......... *G01N 35/00029* (2013.01); *B01L 9/52* (2013.01); *G01N 1/312* (2013.01); *G01N 33/48757* (2013.01); *B01L 2200/025* (2013.01); *B01L 2200/141* (2013.01); *B01L 2200/143* (2013.01); *B01L 2300/0848* (2013.01); *B01L 2300/0858* (2013.01); *G01N 2035/00039* (2013.01); *G01N 2035/00089* (2013.01); *G01N 2035/00138* (2013.01); *G01N 2035/00277* (2013.01); *G02B 21/34* (2013.01)

(58) Field of Classification Search
CPC ..................... G01N 35/0029; G01N 33/48757
See application file for complete search history.

(56) References Cited

U.S. PATENT DOCUMENTS

| | | | | |
|---|---|---|---|---|
| 5,119,573 | A | 6/1992 | Dentella | |
| 5,384,947 | A * | 1/1995 | Kildal | B29O 65/76 |
| | | | | 156/63 |
| 5,674,454 | A * | 10/1997 | Karl | G01N 35/00029 |
| | | | | 206/456 |

(Continued)

FOREIGN PATENT DOCUMENTS

| | | |
|---|---|---|
| EP | 0567067 A1 | 10/1993 |
| EP | 0802413 B1 | 7/2003 |

(Continued)

OTHER PUBLICATIONS

International Search Report and Written Opinion dated May 30, 2016 in corresponding PCT/EP2016/053850 filed Feb. 2016, 12 pages.

*Primary Examiner* — Matthew D Krcha
(74) *Attorney, Agent, or Firm* — Perkins Coie LLP

(57) ABSTRACT

Devices and methods for providing and dispensing opposables onto slides are provided in which magazines loaded with opposables include retention arms to reduce movement of the opposables during shipment and processing and to reduce or eliminate contamination.

20 Claims, 7 Drawing Sheets

(56) References Cited

U.S. PATENT DOCUMENTS

| | | |
|---|---|---|
| 8,911,815 B2 | 12/2014 | Kram et al. |
| 2002/0164235 A1* | 11/2002 | Norris .............. G01N 35/00029 414/331.04 |
| 2004/0092024 A1* | 5/2004 | Reinhardt ................ B65H 1/08 436/43 |
| 2004/0208785 A1* | 10/2004 | Seto ................ G01N 33/48757 422/400 |
| 2005/0106069 A1* | 5/2005 | Matsumoto ............ G01D 11/24 422/98 |
| 2008/0164280 A1* | 7/2008 | Kuriger ............ G01N 33/48757 221/135 |
| 2010/0008824 A1* | 1/2010 | Rich ................ G01N 35/00029 422/63 |
| 2013/0052331 A1 | 2/2013 | Kram et al. |
| 2013/0203100 A1 | 8/2013 | Otter et al. |
| 2013/0220156 A1 | 8/2013 | Haas |

FOREIGN PATENT DOCUMENTS

| | | |
|---|---|---|
| EP | 1480036 | 11/2004 |
| WO | 03/091137 A | 11/2003 |
| WO | 2005057170 | 6/2005 |
| WO | 2014102160 A1 | 7/2014 |

* cited by examiner

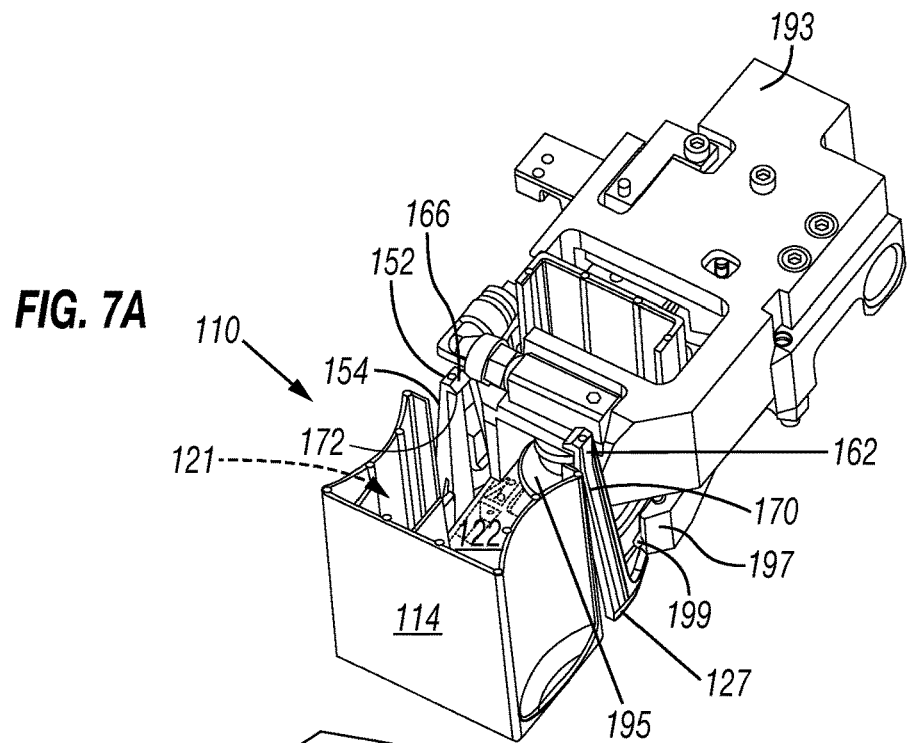
FIG. 7A
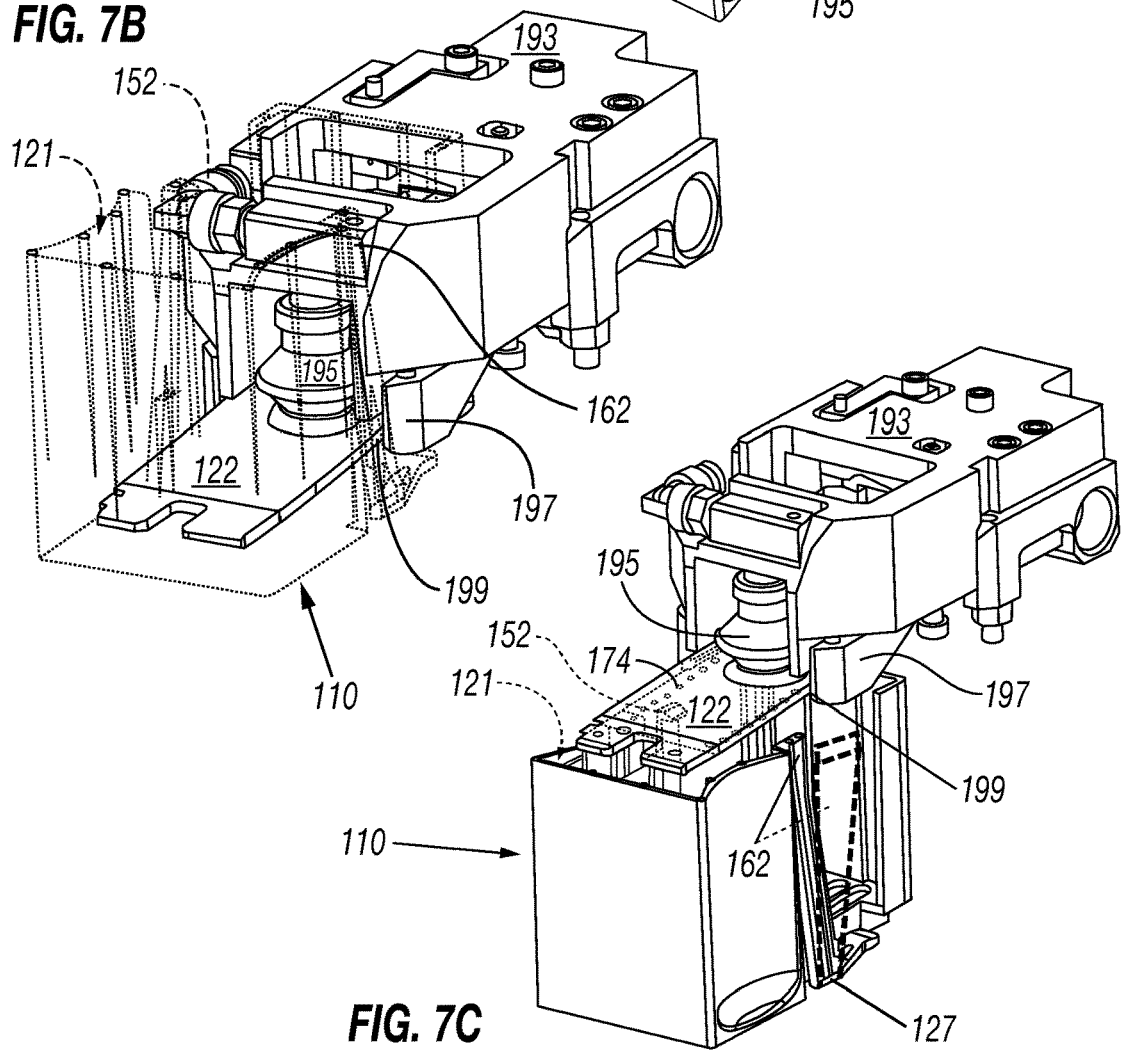
FIG. 7B
FIG. 7C

ASSAY REACTION CONTROLLER MAGAZINE

RELATED APPLICATION DATA

This is a continuation of International Patent Application No. PCT/EP2016/053850, filed Feb. 24, 2016, which claims priority to and the benefit of U.S. Provisional Patent Application No. 62/126,283, filed Feb. 27, 2015, both of which related applications are incorporated by reference herein.

BACKGROUND

Covers for slides (coverslips) are known in the industry for protecting stained samples on microscope slides. When used on automated coverslipping devices the coverslips are often provided in a prepackaged group from a manufacturer and typically are handled manually by a technician. During shipment the coverslips are susceptible to shifting, misalignment and deformation. Later, when automatedly applied to a slide more than one coverslip may be picked up as a result of shifting, static electricity and the like. This can lead to the formation on bubbles or other irregularities which can make microscopic examination of the sample difficult.

Additionally, analytical assay devices having opposing internal surfaces for performing capillary immunohistochemical (IHC), in situ Hybridization (ISH) and staining are also known and packaged similarly as coverslips. When used in automated systems the precise positioning of the assay devices in a retaining device or magazine is important for proper pick up and distribution.

Published applications US20130052331 A1 and US20130203100 A1 disclose a rectangular analytical reaction or assay devices that also have curved or arcuate surfaces. These devices are used to create a capillary gap and spread fluids through this gap across the surface of a microscope slide which contains a biological sample thereon. WO2014/102160 A1 discloses an automated system using such a device and the robotic systems employed for placement of the reaction devices. As mentioned above it is important that the retaining magazines for these reaction devices present each reaction device therein to the robotic pick up device in an aligned and individual manner.

What is described and claimed herein is a system for protecting stacked devices, such as coverslips, capillary reaction devices, microscope slide, etc., hereafter opposables, from shifting and deformation during shipping and processing. Furthermore, such a system is needed to enable the automated dispensing of individual opposables onto slide processing stations and for controlling on-slide fluid distribution to achieve superior staining results without contamination. The system should be economical to manufacture, and it should be simple, effective, and reliable to use.

BRIEF SUMMARY OF THE DISCLOSURE

The present disclosure relates in general to systems, devices, and processes for delivering slides, coverslips, flat reactions devices, curved, rectangular shape reaction devices, etc.—all also known herein as an opposable, or opposables—to specimen processing stations for use with specimen-bearing slides. Opposables can be single use, e.g., disposable, or multi-use devices.

The opposables can be used by automated specimen processing stations to manipulate and direct a series of liquids to specimens. The liquids may be manipulated over or across slide surfaces in conjunction with capillary action while the specimen processing stations control the movement of the opposables and the processing temperatures for histology staining, immunohistochemical staining, in situ hybridization staining, or other specimen processing protocols.

In some embodiments, the opposables are surfaces or opposable elements capable of manipulating one or more substances on a slide. Manipulating a substance in the form of a fluid can include spreading the fluid, displacing a thin film of fluid, or otherwise altering a bolus of fluid, a band of fluid, or a thin film onto the specimen-bearing slides.

By way of example, in one embodiment according to the present disclosure, an opposable magazine is provided with retention arms to maintain optimal alignment of a stack of opposables for transference to slide processing stations while simultaneously reducing or eliminating contamination. The magazine may be designed to be loaded only one way into a magazine fascia or opposable bay. The opposable bay pushes the magazine to a departure stage for distribution via a slide transfer head to individual slide processing stations. Once at the departure module, in one aspect of the disclosure, the retention arms of the magazine are retracted to permit an overhead robot or slide transfer assembly to access a top surface of each opposable.

In another aspect of the disclosure, a magazine for dispensing opposables onto slides may include a magazine floor; a dispensing end wall depending from the magazine floor; an alignment end wall depending from the magazine floor, the alignment end wall spaced apart from the dispensing end wall; a first side wall disposed substantially perpendicular to the alignment end wall and to the dispensing end wall; a second side wall disposed substantially perpendicular to the alignment end wall and to the dispensing end wall, the dispensing end wall, the alignment end wall, the first side wall, and the second side wall forming a bay therebetween for holding an opposable; and at least one retention arm depending from the magazine floor, the retention arm having a proximal end in connection with the magazine floor, the retention arm further comprising a joint and being bendable proximate the joint to release the opposable from the bay. The retention arm may include a guidepost, the joint being bendable away from the guidepost.

The magazine floor may include an aperture for access to an opposable by an ejection device. In this aspect, the ejection device may push the opposable in a direction of the distal end of the retention arm. Further, the magazine floor may include a gripping surface configured to minimize lateral movement of an opposable in the bay. The magazine floor may also include a trough configured to prevent a vacuum seal from developing between an opposable and the magazine floor.

Also according to the aspect of the disclosure, a rib or joist may depend from the dispensing end wall, the alignment end wall, the first side wall, and/or the second side wall in a direction of the bay. The distal end of the retention arm may overhang or extend across a portion of the top most opposable. Further, the distal end of the retention arm may be substantially coterminous with the first and second side walls.

The alignment end wall may include a keying feature complementary in shape to the opposable to facilitate loading of the bay.

The magazine floor may further include a feed aperture configured to receive an ejector therethrough to urge the opposable in a direction away from the magazine floor. The magazine in this aspect may also include a load monitoring tag for identifying a presence of the opposable.

In another aspect of the disclosure, a method for dispensing an opposable from a cartridge may include providing a magazine for holding a plurality of opposables, the magazine having a retention arm, the retention arm, when in a first resting state, being configured to restrict movement of the plurality of opposables in the magazine; positioning a pick-up device proximate a topmost opposable in the magazine, wherein the pick-up device is configured to take up the topmost opposable when engaged therewith; retracting the retraction arm to a second retracted state; activating the pick-up device to engage and retain the topmost opposable; raising the pick-up device with the topmost opposable engaged therewith; and removing the topmost opposable from the magazine.

In this exemplary method, a first portion of the retention arm may bend or rotate away from the plurality of opposables while a second portion maintains contact with the plurality of opposables.

The magazine may include at least two retention arms disposed apart from each other and positioned around or in close proximity to the plurality of opposables.

The topmost opposable in this aspect may be removed from a departure end of the magazine.

The method may also include positioning a control arm to engage a shoulder of the retention arm, engaging the shoulder with the control arm, and retracting the retraction arm to the second retracted state.

In this aspect, the retention arm may be configured such that upon release of the control arm, the retention arm returns to the first resting state, or the control arm may be reversed to return the retention arm to the first resting state.

The method may further include positioning a compression structure to engage a magazine portion proximate the retention arm, a compression gap being formed therebetween, engaging the magazine portion, and reducing the compression gap to retract the retraction arm to the second retracted state.

The method may further include transporting the topmost opposable to a microscope slide.

The method may further include sending an alert as the plurality of opposables in the magazine is expended.

Additional aspects of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the disclosure without departing from the spirit and scope of the subject matter. Variations may include, but are not limited to, substitution of equivalent means, features, or steps for those illustrated, referenced, or discussed, and the functional, operational, or positional reversal of various parts, features, steps, or the like. Those of ordinary skill in the art will better appreciate the features and aspects of such variations upon review of the remainder of the specification.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which:

FIGS. 7A-C include isometric and partial phantom views of the opposable magazine and an embodiment of a pick-up device.

DETAILED DESCRIPTION OF THE DISCLOSURE

Figure 1:
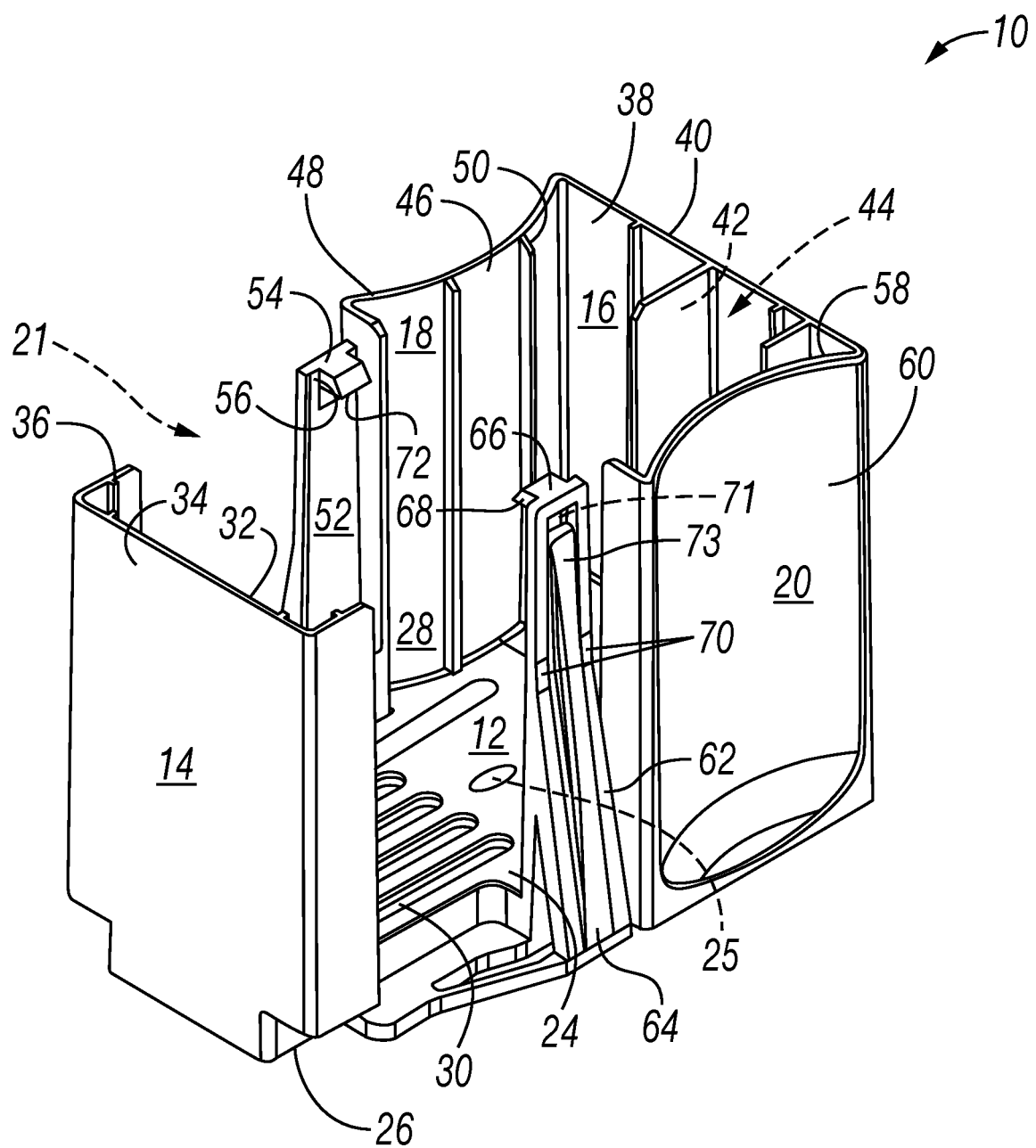
FIG. 1 is a top perspective or isometric view of an opposable magazine according to an aspect of the disclosure.

Detailed reference will now be made to the drawings in which examples embodying the present subject matter are shown. The detailed description uses numerical and letter designations to refer to features of the drawings.

The drawings and detailed description provide a full and written description of the present subject matter, and of the manner and process of making and using various exemplary embodiments, so as to enable one skilled in the pertinent art to make and use them, as well as the best mode of carrying out the exemplary embodiments. However, the examples set forth in the drawings and in the detailed description are provided by way of explanation only and are not meant as limitations of the disclosure. The present subject matter thus includes any modifications and variations of the following examples as come within the scope of the appended claims and their equivalents.

In general, automated systems and methods for selecting opposables or slides from a magazine and for mounting or delivering an opposable on a specimen-bearing microscope slide are provided to minimize damage such as deformation of the opposable and to eliminate or reduce contamination.

More particularly, during a specimen-handling process, slides, slide coverslips, and assay reaction controllers (opposables) or disposable opposables can be provided in a prepackaged stack from a manufacturer or can then be loaded into a magazine. The opposable magazine may hold approximately twenty opposables, although varying quantities are possible. To properly handle the opposables and to reduce the risk of contamination, the magazine is provided with retention arms to contain the opposables. As detailed herein, the retention arms may be manipulated to allow opposable transference to specimen-bearing slides.

Referring now to the figures, FIG. 1 broadly shows an opposable magazine, cartridge or carrier designated in general by the numeral 10. The magazine 10 may include a magazine bottom, floor, or face 12, a departure side or wall 14, an alignment wall or side 16, a first side wall or face 18, and a second side wall or face 20. Together, these form a bay or holding area 21 to receive a load as will be explained herein.

The magazine floor 12 as shown in FIG. 1 includes an inner, interior, or first surface 24 and an outer, exterior or external surface 26. The inner surface 24 may be a gripping surface including a non-slick material, troughs, ridges, or indentations 30 to help maintain a load position, stabilize the load, prevent a vacuum seal from forming between an opposable and the inner surface 24, and prevent lateral or longitudinal shifting movements when the magazine 10 is loaded or moved. A load monitoring tag for identifying a load quantity such as a radio frequency identification (RFID) tag or transmitter 28 also may be embedded in or attached to the interior surface 24 to transmit an alert when the magazine 10 is empty. Alternatively or additionally, the RFID tag 28 may be located in or on one or more of the walls 14, 16, 18, and 20 to send an alert when the magazine 10 is nearing empty. Completing the magazine bottom 12 can be an aperture 25 formed through the interior surface 24 and the outer surface 26 of the magazine floor 12. The aperture or opening 25 is provided through the outer surface 26 extending into the magazine 10 to permit ejection or sequential feeding of a cartridge load, as explained in more detail with respect to FIG. 4 below.

With reference to the departure side 14 of the magazine 10 shown in FIG. 1, an interior side 32 having ridges or ribs 36 and an opposing exterior side or wall 34 are provided. The ribs 36 assist in stabilizing a load in the cartridge 10. In this example, the departure side 14 may bend or turn in a direction of the alignment wall 16, and a pair of stabilizing pylons or retention arms 52 and 62 is provided between the walls 14, 16. More particularly, in this example the first retention arm 52 is located between walls 14, 18 and the second retention arm 62 is located between walls 14, 20. As shown, the first retention arm 52 has a distal end 54, also referred to as a finger or grip herein, which extends from a pair of shoulders or recesses 56.

Like the first retention arm 52, the retention arm 62 has a distal end, finger or grip 66 extending from one or more shoulders or recesses 68. The retention arm 62 most clearly shows a proximal end or stand assembly 64, also referred to herein as a bulwark or base, which includes one or more flexible points, leaf springs, or joints 70. As will be explained in detail with reference to an exemplary operation regarding FIG. 4 below, the joint 70 will bend or rotate away from the bay 21 to allow the grip 66, particularly its contact surface 72 that overhangs the opposables 22 in a resting state, to release an opposable 22 from the bay 21. This is also accomplished by forming a channel or notch 71 in the arms 52, 62 in which respective reeds or guiderails 73 are seated to permit the upper portion of the arms 52, 62 to bend away from the bay 21 while an inner surface of the arms 52, 62 maintains contact with the load in the bay 21. In some embodiments, the joint 70 will have a nominal spring constant to urge the retention arm 62 to its original resting state or position.

As briefly introduced above, FIG. 1 clearly shows the alignment wall 16. The alignment wall 16 has an interior wall or face 38 and an exterior wall or side 40. The face 38 may include a plurality of ribs or ridges 42 that may vary in size and may form an insertion guide or slot 44. As shown, the insertion guide 44 is sized and spaced to accommodate a shaped load such as opposables 22 as shown in FIG. 2 below.

Additionally, FIG. 1 shows that the first side wall 18 includes an interior wall or side 46 having ribs or ridges 50 and an exterior wall or side 48. The ribs 50, like previously introduced ribs 36 and 42, act as point bearing surfaces to assist with controlling or limiting movement of a load while simultaneously minimizing surface contact with the load. Also shown in this example, the exterior wall 48, as well as complementary exterior wall 60, may be concave shaped for gripping and handling as well as serving to increase structural integrity and to further serve as an orientation key such that the magazine 10 cannot be improperly loaded in the bay 21 nor by improperly inserting the magazine 10 into a specimen processing station.

Similar to wall 18, the opposing or second side wall 20 shown in FIG. 1 includes an interior side 58 and the exterior side 60 briefly noted above. Ridges or ribs similar to ribs 50 of side wall 18 are provided on the interior side 58 but are not shown in this view. Together, the floor 12 and the walls 14, 16, 18 and 20 form the bay or cavity 21 for holding a load such as opposables as discussed below.

Figure 2:
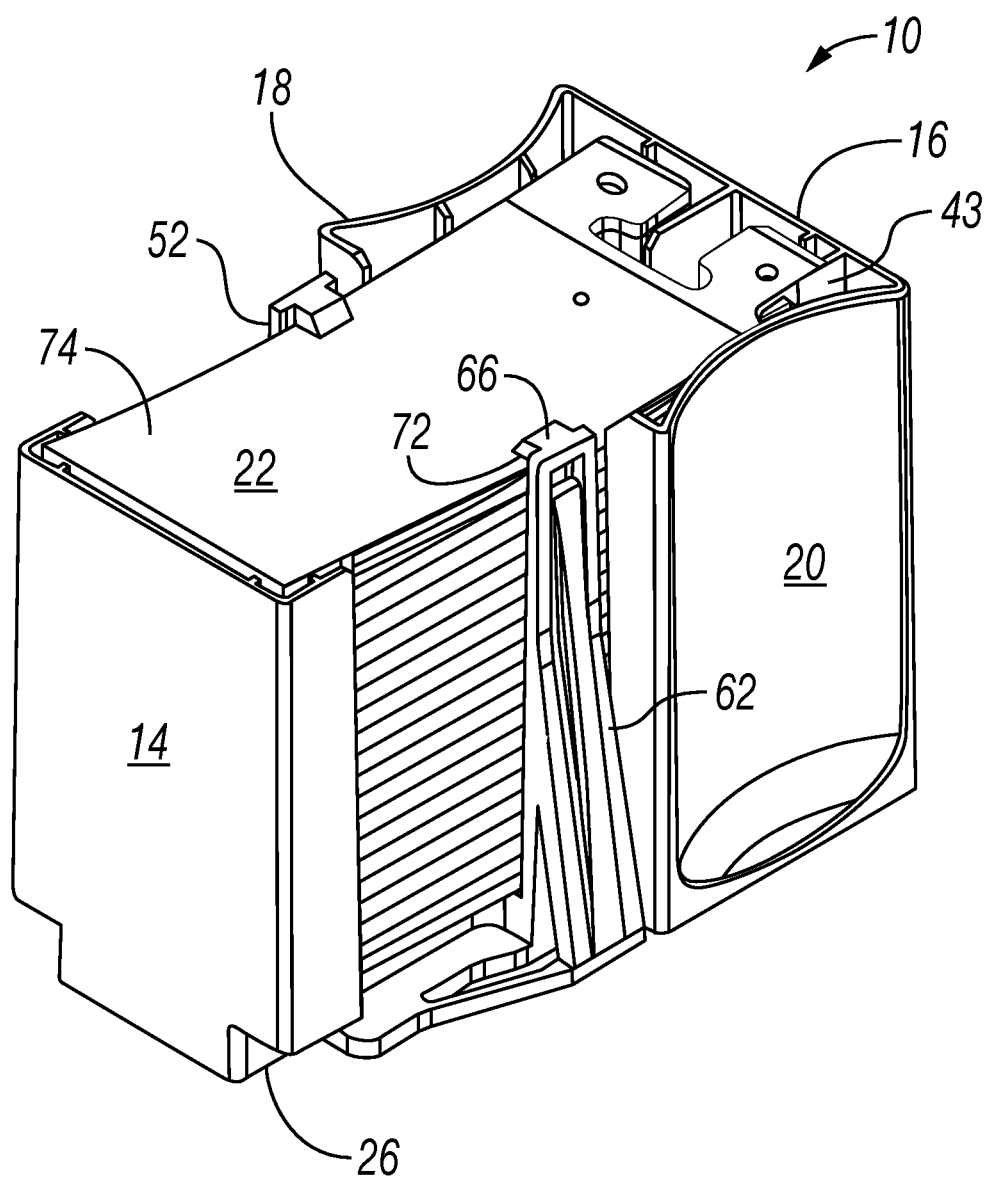
FIG. 2 is an isometric view of the opposable magazine as in FIG. 1, particularly showing the magazine loaded with a plurality of opposables.

Turning now to FIG. 2, the magazine 10 introduced in FIG. 1 is shown loaded with a plurality of disposable opposables or opposables 22 and resting on outer, exterior or external surface 26. Here, the opposables 22 are oriented and loaded between the walls 14, 16, 18 and 20. As shown, an asymmetrical rib feature 43 will interfere with an incorrectly oriented opposable 22 to prevent improper loading of the magazine 10. FIG. 2 particularly shows that the retention arms 52, 62 holding the opposables 22 in position to prevent shifting during shipment, loading and processing. For instance, the contact surface 72 of the grip 66 is mated against a top surface 74 of the uppermost opposable 22 to prevent upward movement of the opposable 22 from magazine 10.

Figure 3:
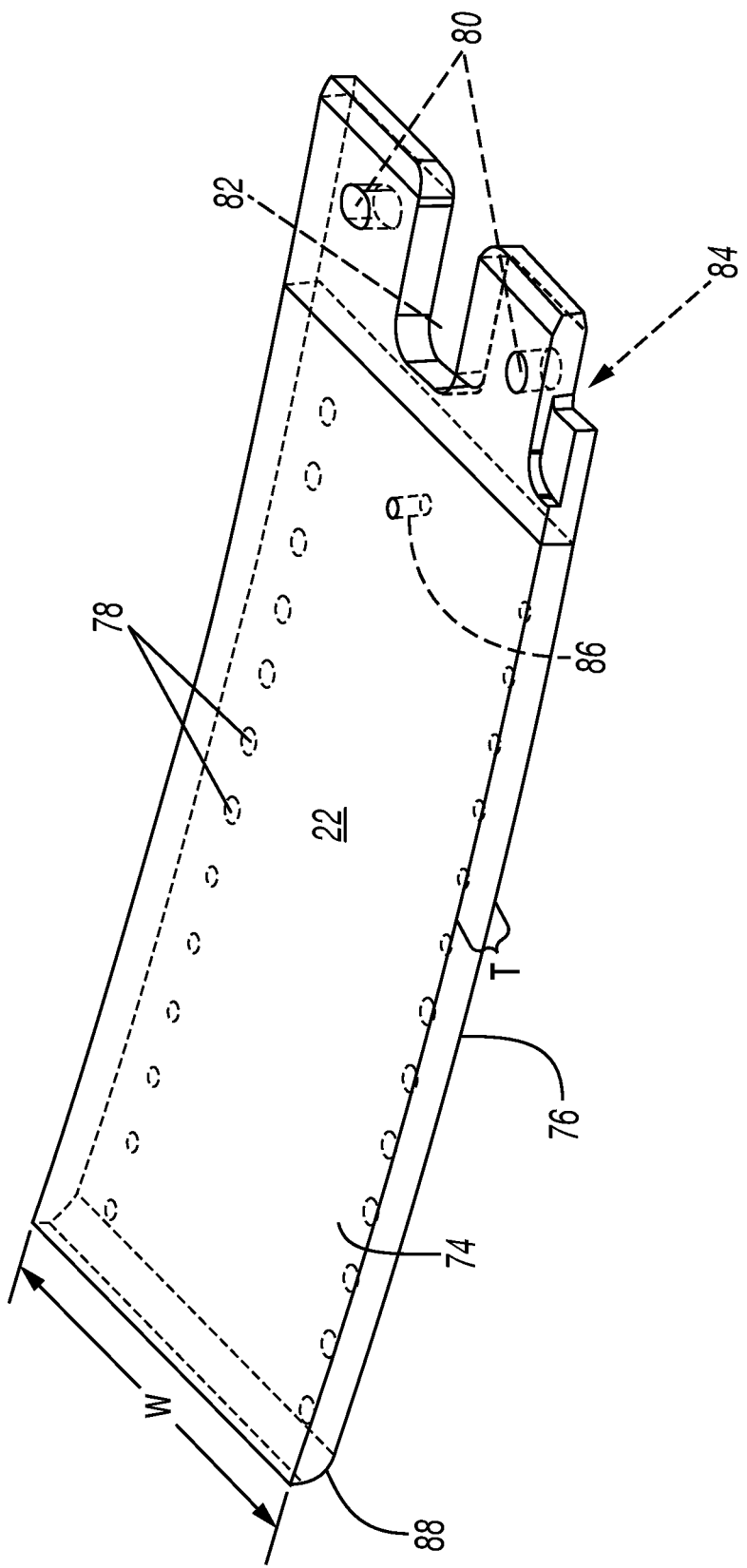
FIG. 3 is an isometric view of an opposable as used in the opposable magazine of FIG. 1.

FIG. 3 most clearly shows an exemplary disposable opposable or opposable 22 introduced above. Here, the opposable 22 includes the top or upper surface 74 and a lower or staining surface or specimen processing region 76. A plurality of gapping features or elements 78 are formed along longitudinal edges of the opposable 22 specimen processing region 76 in this example. The gapping elements 78 can help process a specimen with a desired or minimal amount of fluid. The gapping elements 78 may also be spaced apart from one another to reduce, limit, or substantially prevent wicking between adjacent elements. More specifically, the pattern, number, dimensions, and configurations of the gapping elements 78 can be selected based on the desired interaction between a specimen and a liquid. (See, for example, U.S. Pat. No. 8,911,815 (B2) and WO 2014/102160(A1).) If the opposable 22 includes a field of gapping elements 78, the gapping elements 78 can be distributed evenly or unevenly across the opposable 22 to form different patterns that may include, without limitation, one or more rows, arrays, geometric shapes, or the like.

In the example shown in FIG. 3 the rows of gapping elements 78 extend longitudinally along a length of the opposable 22. The row of gapping elements 78 can include about five gapping elements to about sixty gapping elements with an average distance between adjacent gapping elements in a range of about 0.05 inch (1.27 mm) to about 0.6 inch (15.24 mm). In some embodiments, the row of gapping elements 78 has a zigzag configuration, a serpentine configuration, or other configuration or pattern. Moreover, the gapping elements 78 can be evenly or unevenly spaced from one another. For instance, the distance between adjacent gapping elements 78 can be greater or less than the heights of the gapping elements 78. Other spacing arrangements are also possible, if needed or desired. In some embodiments, the thickness T is about 0.08 inch (2 mm), and a width W can be in a range of about 0.6 inch (15.24 mm) to about 1.5 inch (38 mm). In some embodiments, the width W is about 1.2 inches (30 mm). Still other widths are possible.

With reference now to FIGS. 1, 2 and 3, the alignment features 80, a slot or insertion shoe 82, and a keying feature 84 are formed, sized and shaped to properly align and orient the opposable 22 in the magazine 10. More specifically, the insertion shoe 82 can receive a feature of the magazine 10 such as the interior rib 42 which in part forms the guide 44. The alignment features 80 (e.g., holes, protrusions, etc.) are also used to align the opposable 22. As introduced above, the guide 44 ensures proper alignment and orientation of the opposable 22. The keying feature 84 in particular mates with the rib 43 to ensure correct loading of the magazine 10.

Continuing with specific reference to FIG. 3, a waste port 86 may also be provided through the surface 74 of the opposable 22. Thus, when the staining surface 76 interfaces with or engages a liquid on a slide, the liquid may be removed via the port 86 as shown in this example. Also by way of example, although the opposable 22 shown in FIG. 3 is generally rectangular shaped, the opposable 22 may be generally circular shaped, square shaped, or other suitable shape. In some embodiments, the opposable 22 may be circular with diameters of 18 mm, 22 mm, or 25 mm. Square opposables 22 may have sides with lengths of about 18 mm, 22 mm, or 25 mm. Rectangular opposables 22 may have sides with lengths from about 11 mm×22 mm to about 48 mm×60 mm. The dimensions, shapes, and properties of the opposables 22 may be selected based on, for example, the size of the intended microscope slides. The opposables 22 may be made, in whole or in part, of transparent plastic, glass, or other transparent or semi-transparent materials. Depending on the materials used and intended use, the opposables 22 may be disposed of after one use or a finite number of uses, hence the name "disposable opposables".

In a further aspect of the disclosure as shown in FIG. 3, the opposables 22 may have a substantially planar top and bottom surface and a substantially rectangular configuration, with a length and a thickness slightly less than a specimen slide. Here, the bottom surface 76 of the opposable 22 may define or express a curvature terminating in a gradually angled or curving end 88 positioned to captivate a band of liquid such that when the opposable 22 is over-rolled, a band of liquid can contact and cling to the tapered region 88. Specifically, the tapered area 76 is a liquid captivation feature. The tapered region 76 provides a large surface area to which the liquid can cling. The illustrated tapered region 76 also may have a radius of curvature equal to or less than about 0.08 inch to cooperate with a standard microscope slide to captivate a band of liquid on the surface of the slide and help prevent "wicking" of the fluid therefrom. Other radii of curvature can be used, if needed or desired. In some embodiments, the curvature of the rounded edge 88 is uniform across the width W of the opposable 22. In other embodiments, the curvature of the rounded edge 88 varies across the width W of the opposable 22.

Figure 4:
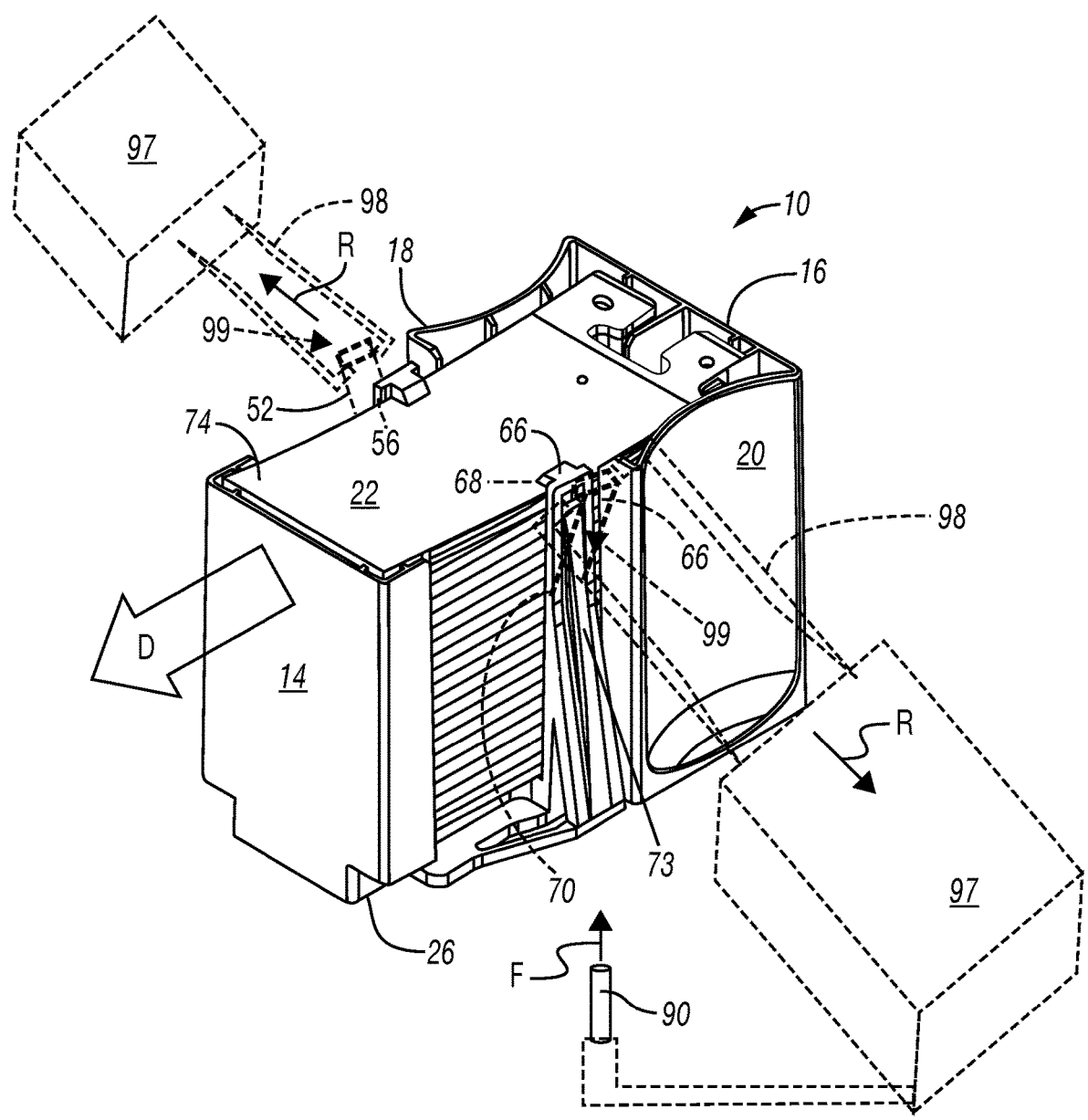
FIG. 4 shows retraction arms (in phantom) manipulating magazine arms according to one aspect of the disclosure.

FIG. 4 shows an exemplary operation in which the opposable magazine 10 is employed in an intended environment. As shown, programmable logic controlled (PLC) machinery or a retraction robot assembly 97 may include in an exemplary embodiment one or more retraction or control arms 98. The control arms 98 are configured to engage the respective shoulder areas 56, 68 of the retention arms 52, 62. As shown for instance (in phantom for clarity) at arm 62, when the retraction arms 98 are pulled back or retracted by the robot 97 (indicated by arrow R), the arm 62, which is initially in a first state or resting condition, will bend at or rotate about a joint 70 to retract finger 66 away from the surface 74 of the topmost opposable 22 as indicated by a second state or condition 99 shown phantom for clarity. The foregoing process also occurs with the retention arms 52. During this process, guidepost 73 remains seated against or in contact with an edge of the opposable load. Thus, the topmost opposable 22 may be picked up from the departure end of wall 14 indicated by arrow D. The retention arms 52, 62 may have a nominal spring constant such that when the retraction arm(s) 98 reverses direction R, the finger 66 is urged to return to its first resting state and reengage or overhang the next surface 74 of the next opposable 22 to prevent load slippage until the subsequent opposable 22 is required. Alternatively, the arms 98 may actively push or reposition the retention arms 52, 62 proximate the surface 74 of the subsequent opposable 22.

FIG. 4 further shows an ejector device, pin or push assembly 90 located under the magazine 10. The assembly 90 may be controlled by the retraction robot assembly 97. In one embodiment, the assembly 90 will be positioned and activated approximately simultaneously during retraction of the retention arms 52, 62 by the retraction arm(s) 98. Here, the push assembly 90 projects through the aperture 25 formed through the outer surface 26 and the interior surface 24 of the magazine floor 12 (see FIG. 1). Thus, the push assembly 90 will individually or sequentially push or feed the plurality of opposables 22 in a direction of the fingers 54, 66 as indicated by feed arrow F.

Figure 5:
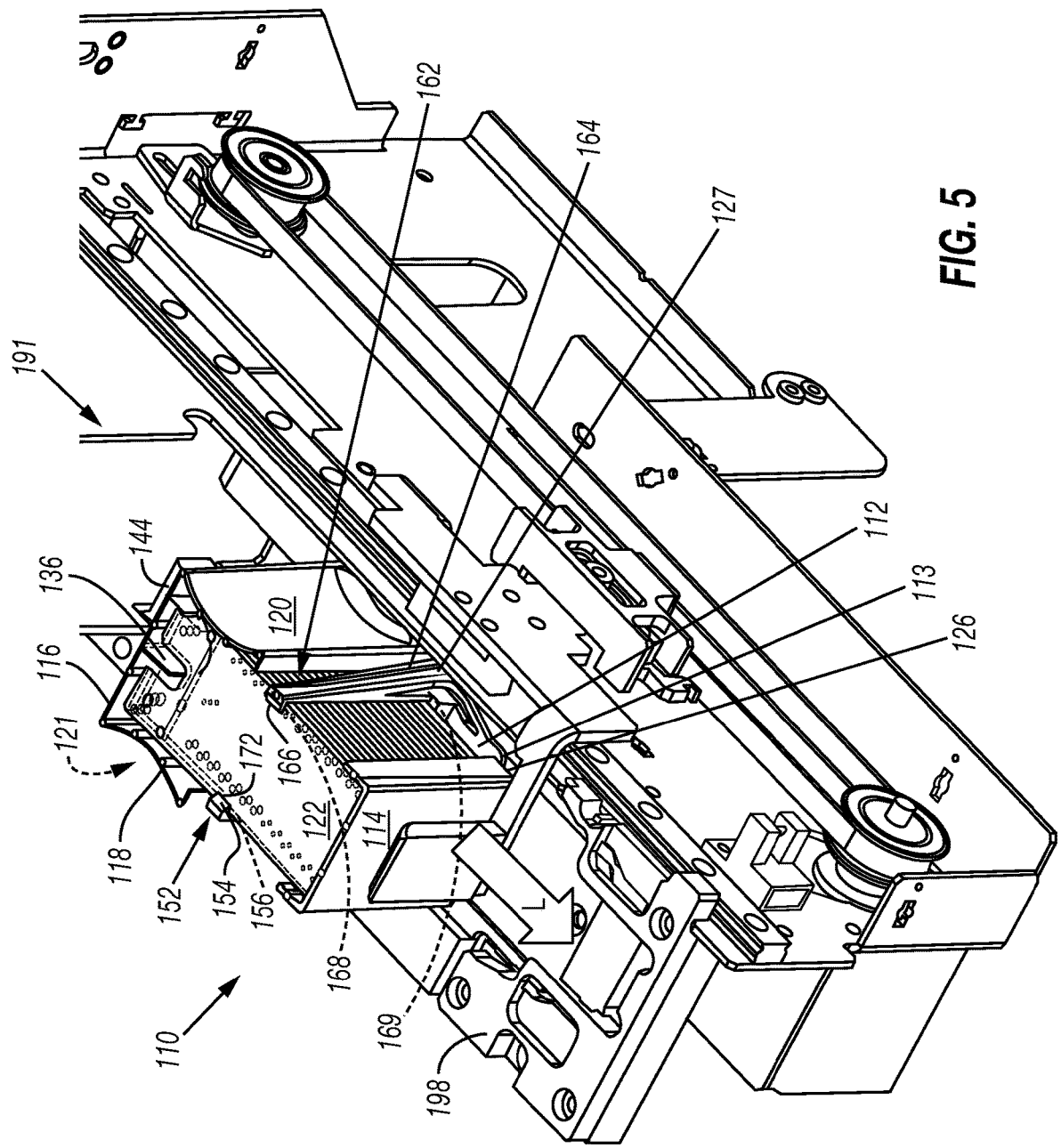
FIG. 5 is an isometric view of an opposable magazine in an intended use environment according to another aspect of the disclosure.

With reference now to FIG. 5 in accordance with another aspect of the disclosure, an opposable magazine, cartridge, or carrier is designated in general by the numeral 110 and positioned on a processing station or opposable selection device 191. The magazine 110 broadly includes a magazine bottom, floor, or face 112, an extraction or departure side or wall 114, an alignment wall or side 116, a first side wall or face 118, and a second side wall or face 120. Together, these form a bay or holding area 121 to receive a load of assay reaction controllers (opposable) or disposable opposables 122.

The magazine floor 112 shown in FIG. 5 includes an inner, interior, or first surface and an outer, exterior or external surface 126. The inner surface may include a gripping surface including a non-slick material, troughs, ridges, or indentations to help maintain a load position, stabilize the load, prevent a vacuum seal from forming between an opposable and the floor 112, and to prevent lateral or longitudinal shifting movements when the magazine 110 is loaded. A load monitoring tag for identifying a load quantity such as a radio frequency identification (RFID) tag or transmitter also may be embedded in or attached to the interior surface of the floor 112 to transmit an alert when the magazine 110 is empty. Alternatively or additionally, the RFID tag may be located in or on one or more of the walls 114, 116, 118, and 120 to send an alert when the magazine 110 is nearing empty. The RFID may monitor load weight and/or a counting read/write system may track each consumable extraction to determine the remaining load.

As FIG. 5 further shows, a plurality of ridges or ribs 136 may be provided along interior areas of the walls 114, 116, 118, and 120. The ribs 136 assist in stabilizing a load in the cartridge 110. The ribs 136 may vary in width (depth) and height and may form an insertion guide or slot 144 to dictate correct orientation and proper loading of a shaped load such as opposables 122. As shown, the insertion guide 144 is sized and spaced to accommodate complementary shaped opposables 122.

Also shown in the example of FIG. 5, the departure side 114 may be formed with a bend or turn in a direction of the alignment wall 116 to help secure the opposables 122 in the bay 121. Moreover, a pair of stabilizing pylons or retention arms 152 and 162 may be provided between the walls 114, 116 to secure the opposables 122. Here, the first retention arm 152 is located between walls 114, 118. The second retention arm 162 is located between walls 114, 120 also to stabilize and secure the opposables 122 in the bay 121.

Figure 6:
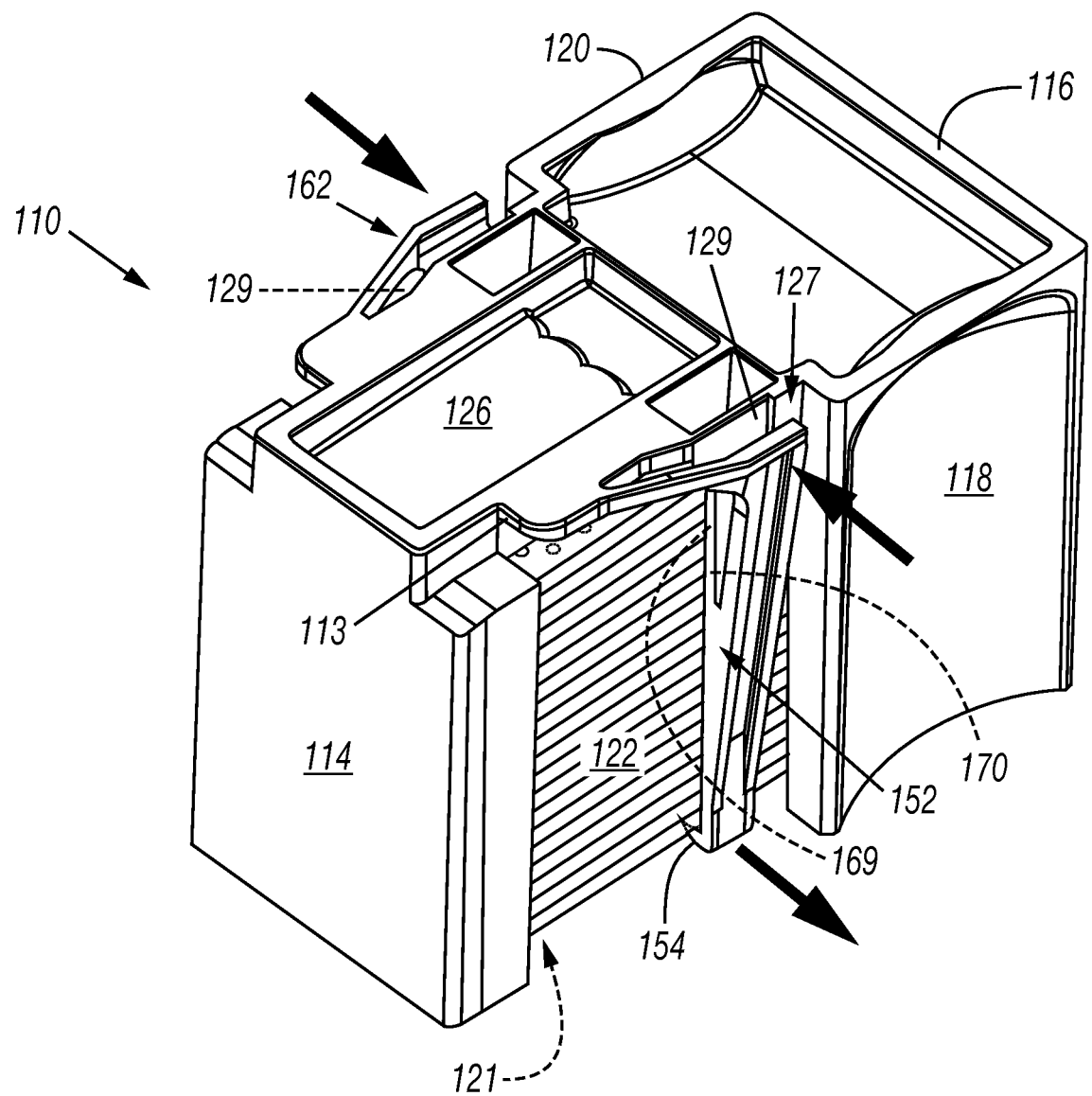
FIG. 6 is a bottom isometric view of the opposable magazine as in FIG. 5 loaded with opposables, particularly showing a release feature of the magazine.

With reference to FIGS. 5 and 6, the first retention arm 152 has a finger, grip or distal end 154, which extends from a pair of shoulders or recesses 156. Likewise, the second retention arm 162 has a distal end, finger or grip 166 that extends from one or more shoulders or recesses 168. As shown, in a first or resting state, the surface 172 of the grip 166 overhangs, or is in resting contact with, the topmost opposable 122. This example also shows that the retention arm 162 includes a proximal end, bulwark, base or stand assembly 164, which includes one or more compression features, gaps or apertures 169 that form flexible points or joints 170.

As best shown from the perspective of the arm 162 in FIG. 5, on either side of the magazine 110 is a compression structure 127 that depends at an angle from the floor 126 and includes a lateral gap or opening 129 (see FIG. 6) in connection with the compression aperture 169 in the base 164. The lateral opening 129 and the compression aperture 169 form a leaf spring arrangement as described in further detail below with respect to FIG. 6. Also shown, a stop or shoulder 113 may be formed at or near the floor 126 to secure the magazine 110 in position during unloading.

The compression structure 127 of the magazine 110 is most clearly shown from a bottom perspective in FIG. 6. The sliding engagement L of the magazine 110 with a complementary angled compression structure 198 noted above with respect to FIG. 5 causes the shoulder 113 to hold the magazine 110 in position on the selection device 191 while the lateral gap 129 and the compression gap 169 close in a direction of the bay 121, as indicated by the inwardly directed arrows shown in FIG. 6. This in turn causes the joint 170 to bend and to push the arms 152, 162 away from the bay 121 as indicated by the outward arrow.

Turning now to FIGS. 7A-7C, by way of exemplary operation, a portion of a pick-up device 193 is positioned above the magazine 110. As the magazine 110 is moved in a loading direction L (see FIG. 5) toward a slide processing station (not shown), the compression structure 198 (see FIG. 5) engages the compression structure 127 of the magazine 110. The sliding engagement causes the lateral gap 129 and the compression gap 169 noted in FIG. 6 to close in a direction of the bay 121. This in turn causes the joint 170 to rotate and to push the arms 152, 162 away from the bay 121 to allow the grip 166, particularly its opposable holding surface 172, to release an opposable 122 from the bay 121.

FIGS. 7B & 7C further show that as the arms 152, 162 are retracted away from the bay 121 in a second or tensioned state (in phantom), a pick-up device 195, such as a suction cup or lifter head, is extended or lowered to a surface of the topmost opposable 122 in the bay 121. Alternatively, or additionally, the opposable 122 may be spring-loaded and pushed upward to meet the pick-up device 195. Once suction is applied and the device 195 is in suction contact with and has control of the topmost opposable 122 via the surface 174, the topmost opposable 122 is removed from the magazine 110. Each subsequent opposable 122 may be removed by the same or another pick-up device 195 until the magazine 110 is empty and a subsequent magazine is loaded via the magazine fascia of a slide processing station. Alternatively, the direction L of the magazine 110 may be reversed and/or the compression structure 198 (compare FIG. 5) may be disengaged between each opposable 122 to return the arms 152, 162 to their resting state between opposable 122 extractions.

Also shown in FIGS. 7A-C, the suction head 195 is placed into suction contact with one of the opposables 122 in the bay 121. A lifter arm 197 having a finger, shelf, or underlying protrusion 199 also may be pressed into contact with or be closed about a portion of a perimeter of the opposable 122 to assist the suction head 195 in securing the opposable 122 to lift it from the bay 121, as indicated by the double-headed arrow.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

The invention claimed is:

1. A magazine for dispensing opposables configured to cover slides, the magazine comprising: a magazine floor;
   a dispensing end wall depending from a first end of the magazine floor; an alignment end wall depending from a second end of the magazine floor opposite the first end;
   a first side wall depending from the magazine floor and extending in a substantially perpendicular direction from the alignment end wall toward the dispensing end wall to an intermediate position between the alignment end wall and the dispensing end wall; a second side wall depending from the magazine floor and extending in a substantially perpendicular direction from the alignment end wall toward the dispensing end wall to an intermediate position between the alignment end wall and the dispensing end wall, wherein the dispensing end wall, the alignment end wall, the first side wall, and the second side wall form a bay therebetween for holding a stack of opposables;
   a guidepost depending from the magazine floor; and
   a first retention arm depending from the magazine floor and positioned between the dispensing end wall and the first side wall, the first retention arm including
      a proximal end in connection with the magazine floor and
      a joint,
   wherein a connection of the guidepost to the magazine floor is within the proximal end of the first retention arm and the guidepost is configured to contact a side of the stack of opposables at the bay;
   wherein a portion of the first retention arm is bendable proximate the joint to release one of the opposables from the bay to allow removal of the one of the opposables from the stack while the guidepost contacts substantially the entire height of the stack of opposables held in the bay.

2. The magazine of claim 1, wherein the magazine floor includes an aperture defined therethrough for access to the opposable by an ejection device, the ejection device configured to push the opposable in a direction of the distal end of the first retention arm.

3. The magazine of claim 1, wherein the magazine floor includes a gripping surface configured to minimize lateral movement of an opposable in the bay.

4. The magazine of claim 1, wherein the magazine floor includes a trough configured to prevent a vacuum seal between an opposable and the magazine floor.

5. The magazine of claim 1, further comprising a rib depending in a direction of the bay from the dispensing end wall, the alignment end wall, the first side wall or the second side wall.

6. The magazine of claim 1, wherein the distal end of the first retention arm overhangs a portion of the top most opposable.

7. The magazine of claim 1, wherein the distal end of the first retention arm is substantially coterminous with the first and second side walls.

8. The magazine of claim 1, wherein the joint is bendable away from the guidepost while the guidepost is biased toward the bay to hold each of the opposables in the stack.

9. The magazine of claim 1, wherein the alignment end wall includes a keying feature complementary in shape to the opposable to facilitate loading of the bay.

10. The magazine of claim 1, wherein the magazine floor includes a feed aperture defined therethrough, the feed aperture being configured to receive an ejector therethrough to urge the opposable in a direction away from the magazine floor.

11. The magazine of claim 1, further comprising a load monitoring tag for identifying a presence of the opposable.

12. The magazine of claim 1, further comprising a second retention arm depending from the magazine floor and positioned between the dispensing end wall and the second side wall, the second retention arm having a proximal end in connection with the magazine floor.

13. The magazine of claim 12, wherein the first and second retention arms are configured to interface with opposite sides of a perimeter of the opposable.

14. A magazine for dispensing opposables in a stacked configuration, the magazine comprising:
  a magazine floor;
  a dispensing end wall extending from a first end of the magazine floor;
  an alignment end wall extending from a second end of the magazine floor opposite the first end, the alignment end wall having an insertion guide projecting toward the dispensing end wall and configured to be received within a slot on a perimeter of an opposable;
  a first side wall extending partially from the alignment end wall to the dispensing end wall, forming a first gap between the first side wall and the dispensing end wall;
  a second side wall extending partially from the alignment end wall to the dispensing end wall, forming a second gap between the second side wall and the dispensing end wall, wherein the magazine floor, the dispensing end wall, the alignment end wall, the first side wall, and the second side wall together define a bay therebetween for holding the opposables; and
  a first retention arm extending from the magazine floor within the first gap,
  the first retention arm including
    a bendable joint configured to deflect such that the first retention arm releases one or more of the opposables from the bay,
    a proximal end connected to the magazine floor, and
    a guidepost having a connection extending from the magazine floor and being part of the proximal end of the first retention arm, wherein the guidepost is configured to contact the opposables in the stack held in the bay while a portion of the first retention arm is deflected away from the stack to remove the one or more opposables from the stack.

15. The magazine of claim 14, further comprising a second retention arm extending from the magazine floor within the second gap and positioned opposite the first retention arm.

16. The magazine of claim 15, wherein the first and second retention arms are configured to interface with opposite sides of a perimeter of the opposable.

17. The magazine of claim 14, wherein the magazine floor includes an aperture defined therethrough for access to the opposable by an ejection device, the ejection device configured to push the opposable in a direction of the distal end of the first retention arm.

18. The magazine of claim 14, wherein the magazine floor includes a trough configured to prevent a vacuum seal between an opposable and the magazine floor.

19. The magazine of claim 14, wherein the distal end of the first retention arm overhangs a portion of the top most opposable.

20. The magazine of claim 14, wherein the joint is bendable away from the guidepost while the guidepost is biased against substantially an entire height of the stack.

\* \* \* \* \*